US00PP18536P2

(12) United States Plant Patent
Carruth

(10) Patent No.: US PP18,536 P2
(45) Date of Patent: Mar. 4, 2008

(54) HYBRID TEA ROSE PLANT NAMED 'WEKRIGOYELO'

(50) Latin Name: *Rosa hybrida*
Varietal Denomination: WEKrigoyelo

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 3 days.

(21) Appl. No.: 11/594,664

(22) Filed: Nov. 6, 2006

(51) Int. Cl.
*A01H 5/00* (2006.01)

(52) U.S. Cl. ..... Plt./137

(58) Field of Classification Search ..... Plt./137
See application file for complete search history.

(56) References Cited

U.S. PATENT DOCUMENTS

2003/0115644 P1 * 6/2003 Rosenberg ..... Plt./137

* cited by examiner

*Primary Examiner*—Wendy Haas
(74) *Attorney, Agent, or Firm*—Christie, Parker & Hale, LLP.

(57) ABSTRACT

A new variety of Hybrid Tea rose suitable for garden decoration, having flowers of vibrant pink with a golden glow coloration.

1 Drawing Sheet

Classification: The present invention relates to a new *Rosa hybrida* plant.

Variety denomination: The new plant has the varietal denomination 'WEKrigoyelo'.

BACKGROUND OF THE INVENTION

This invention relates to a new and distinct variety of Hybrid Tea Rose. It has as its seed parent the variety known as 'DORviso' (not patented) and has an undisseminated seedling of my creation as its pollen parent with the following genetic origin Seedling×'O Sole Mio'.

SUMMARY OF THE INVENTION

Among the features which distinguish the new variety from other presently available and commercial rose cultivars known to the inventor are the following combination of characteristics: its peduncle bearing long prickle-like stipitate glands, its bud surface bearing few long foliaceous appendages, many stipitate glands and hairs and its even vibrant pink with a golden glow flower coloration that lasts throughout the life of the flower. The plant has an upright somewhat spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKrigoyelo' may be asexually propagated by budding and grafting. The budding and grafting successfully occurred on the plant/rootstock *Rosa hybrida* cv. 'Dr. Huey' (unpatented).

COMPARISON WITH PARENTS

The new rose may be distinguished from its seed parent, 'DORviso' by the following combination of characteristics: whereas 'WEKrigoyelo' bears flowers of vibrant pink with a golden glow coloration, 'DORviso' bears flowers of deep pink coloration. The new variety has an upright somewhat spreading medium height growing habit (about 115 to about 140 cm. in height), whereas the seed parent has an upright moderately compact significantly shorter growing habit. 'WEKrigoyelo' bears young leaves of pale green coloration, whereas 'DORviso' bears young leaves of significantly darker olive green coloration.

The new variety may be distinguished from its pollen parent, an undisseminated seedling of my creation by the following combination of characteristics: whereas 'WEKrigoyelo' bears large sized flowers (about 8.2 to about 14.7 cm. in diameter) of vibrant pink with a golden glow coloration, the undisseminated seedling bears significantly smaller flowers (about 5.9 to about 8.4 cm. in diameter) of medium yellow coloration. The new variety is classified as a hybrid tea rose with an upright somewhat spreading medium height growing habit (about 115 to about 140 cm. in height), whereas the pollen parent is classified as a floribunda rose with a rounded and compact significantly shorter growing habit.

COMPARISON WITH THE CLOSEST COMMERCIALLY AVAILABLE CULTIVAR

The closest commercially available cultivar to the new variety is the seed parent 'DORVISO'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety usually bears its flowers singly. Flowers are borne on strong short to medium length stems (about 15 to about 65 cm.). Outdoors, the plant blooms abundantly and nearly continuously during the growing season. The flowers have a slight tea fragrance.

BUD

The peduncle is about 2.3 to about 5.6 cm. in length, of somewhat heavy caliper (about 0.3 to about 0.5 cm. in diameter), and usually erect to moderately stiff. It is rough with many long prickle-like stipitate glands, few hairs and some small prickles. Peduncle color is between 144A and 143A.

Before the calyx breaks, the bud is about 1.1 to about 2.0 cm. in diameter at the widest point, about 1.8 to about 2.7 cm. in length, and pointed in shape. The surface of the bud bears few long foliaceous appendages, many stipitate glands and hairs usually with slender much cut foliaceous parts extending beyond the tip of the bud about ¼ or more of its length. Bud color is between 144A and 143A.

The sepals are about 2.8 to about 4.1 cm. in length and about 0.7 to about 1.3 cm. in width at the widest point. The outer surface color of the sepal is between 144A and 143A. The inner surface color of the sepal is between 137A and 138A and covered with fine wooly tomentum; sepal margins are lined with many stipitate glands and few hairs.

The receptacle of the flower is of very short length (about 0.2 to about 0.4 cm.) and thin in caliper (about 0.4 to about 0.7 cm. in diameter). The receptacle is usually nearly flat to sometime somewhat rounded in form. Its surface is moderately smooth with few hairs and stipitates glands and with thin fleshy walls. The receptacle color is between 144A and 143A.

As the petals open (after the calyx breaks), the bud is about 2.5 to about 3.4 cm. in diameter at the widest point, about 2.8 to about 3.8 cm. in length, and moderately ovoid to somewhat pointed in form. The color of the under and upper surfaces of the newly opened petals is between 53B and 47B. At the point where the petal attaches on the under surface of the newly opened petals, there is a moderately small zone of between 3C and 4B. At the point where the petal attaches on the upper surface of the newly opened petals, there is a large zone of between 4A and 5C.

BLOOM

When fully open, the bloom ranges from about 8.2 to about 14.7 cm. in diameter. Petalage is double with about 23 to 30 petals and about 1 to 5 petaloids irregularly arranged. When partially open, the bloom form is high centered to somewhat cupped, and the petals are moderately tightly spiraled to cupped with petal edges slightly reflexed outward. When fully open, the bloom form is cupped and the petals are loosely cupped to somewhat undulated with petal edges moderately reflexed outward.

PETALS

The substance of the petals is moderately heavy and of medium to somewhat thick thickness, with upper surfaces moderately satiny and under surfaces slightly shiny to matte. The petals are about 3.7 to about 5.9 cm. in length and about 3.3 to about 6.7 cm. in width at the widest point. Petal margins are entire.

The outer petals are nearly round in shape with rounded apices.

The inner petals are broadly obovate in shape with rounded apices.

Petaloids are about 1.4 to about 3.4 cm. in length and about 0.9 to about 1.8 cm. in width at the widest point. Petaloids are irregularly shaped sometimes nearly rounded and sometimes somewhat oblanceolate with rounded apices.

NEWLY OPENED FLOWER

The under and upper surface color of the outer petals is between 63B and 58C. At the point where the petal attaches on the under surface there is a moderately small zone of between 5C and 6C. At the point where the petal attaches on the upper surface there is a large zone of between 6C and 7C.

The under and upper surface color of the intermediate and inner petals is between 58B and 51A.

The under and upper surface color of the petaloids are similar in coloration to the upper and under surfaces of the intermediate and inner petals.

The general tonality of the newly opened flower is between 58B and 51A.

THREE-DAY-OLD FLOWER

The under and upper surface color of the outer petals is between 63B and 61D sometimes fading to between 68C and 62B on the outer edge of the outer most petals. At the point where the petal attaches on the under surface there is a moderately small zone of between 5C and 6C. At the point where the petal attaches on the upper surface there is a large zone of between 6C and 7C.

The under and upper surface color of the intermediate and inner petals is between 63B and 61D.

The under and upper surface color of the petaloids are similar in coloration to the upper and under surfaces of the intermediate and inner petals.

The general tonality of the three-day-old flower is between 63B and 61D.

On the spent bloom, the petals usually drop off cleanly.

In September in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 135) and are arranged regularly about the pistils; a few are mixed with petaloids. The filaments are of irregular length (about 0.4 to about 1.4 cm.) most with anthers. Filaments are between 13B and 14B in color often moderately suffused with between 44B and 33B. The anthers are of medium size for the class and all open approximately at the same time. Anther color is between 19A and 16D when immature and between 200A and 163C at maturity. Pollen is abundant and between 15B and 16B in color.

FEMALE REPRODUCTIVE ORGANS

Pistils vary in number (average about 175). The styles are moderately even, somewhat short in length (about 0.4 to about 0.6 cm.), moderately thin in caliper, and separated to loosely bunched. Stigma color is between 17C and 16B. Style color is between 154C and 1C usually heavily suffused with between 53A and 46A. Ovaries are usually all enclosed in the calyx.

Hips have not been observed on this variety when grown in Upland, Calif.

FOLIAGE

The compound leaves are usually comprised of three to seven leaflets and are borne abundantly. The five-leaflet leaves are about 8.4 to about 17.4 cm. in length and about 6.6 to about 12.5 cm. in width at the widest point, moderately thin to somewhat leathery in texture and moderately glossy in finish. The terminal leaflets are about 3.8 to about 8.1 cm. in length and about 2.7 to about 5.5 cm. in width at the widest point, shaped ovate with acute to somewhat acuminate apices and rounded bases. Their margins are usually simply serrate.

The upper surface color of the mature leaf is between 147A and 137A. The under surface color of the mature leaf is between 147B and 138B. The upper surface color of the young leaf is between 146A and 143B, usually heavily suffused with between 187A and 183A. The under surface color of the young leaf is between 146B and 144A, usually heavily suffused with between 187B and 183B.

The rachis is somewhat light to average in caliper and moderately rough. The upper side is somewhat deeply grooved with few hairs and some stipitate glands on the edges of the grooves. The under side of the rachis is moderately rough with few stipitate glands and small prickles. The rachis color is between 145B and 137C sometimes lightly suffused especially on the young leaves with between 187B and 183B.

The stipules are about 1.4 to about 2.1 cm. in length and moderately wide (about 0.5 to about 0.7 cm.) with long straight points that usually turn out at an angle of more than 45 degrees and sometimes recurve toward the stem. The stipules color is between 146C and 137C.

The petiole is somewhat light to average in caliper and moderately rough. The upper side is somewhat deeply grooved with few hairs and some stipitate glands on the edges of the grooves. The under side of the petiole is moderately rough with few stipitate glands and small prickles. The petiole is about 0.6 to about 2.0 cm. in length and about 0.1 to about 0.2 cm in diameter at the widest point. The petiole color is between 145B and 137C sometimes lightly suffused especially on the young leaves with between 187B and 183B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright somewhat spreading medium height growing habit (about 115 to about 140 cm. in height and about 66 to about 85 cm. spread at the widest point), with full branching. It displays moderately vigorous growth and the canes are of medium to somewhat light caliper for the class.

The color of the major stems is between 146B and 147B. They bear many large prickles that are about 1.1 to about 1.4 cm. in length. The large prickles are almost straight and angled slightly downward with a long narrow oval base; prickle color is between 165B and 177B. The major stem bears few small prickles of similar shape and coloration.

The color of the branches is between 146C and 137C. They bear some large prickles which are of similar size and shape to the large prickles on the major stems; prickle color is between 1C and 2C. The branches bear few small prickles of similar shape and coloration.

The color of the new shoots is between 146C and 143C sometimes lightly suffused with between 187C and 183C. They bear few large prickles which are of similar size and shape to the large prickles on the major stems; prickle color is between 145A and 145B often heavily suffused with between 183D and 187D. The shoots bear many small prickles of similar shape and coloration.

What is claimed is:

1. A new and distinct Hybrid Tea rose plant of the variety substantially as described and illustrated herein.

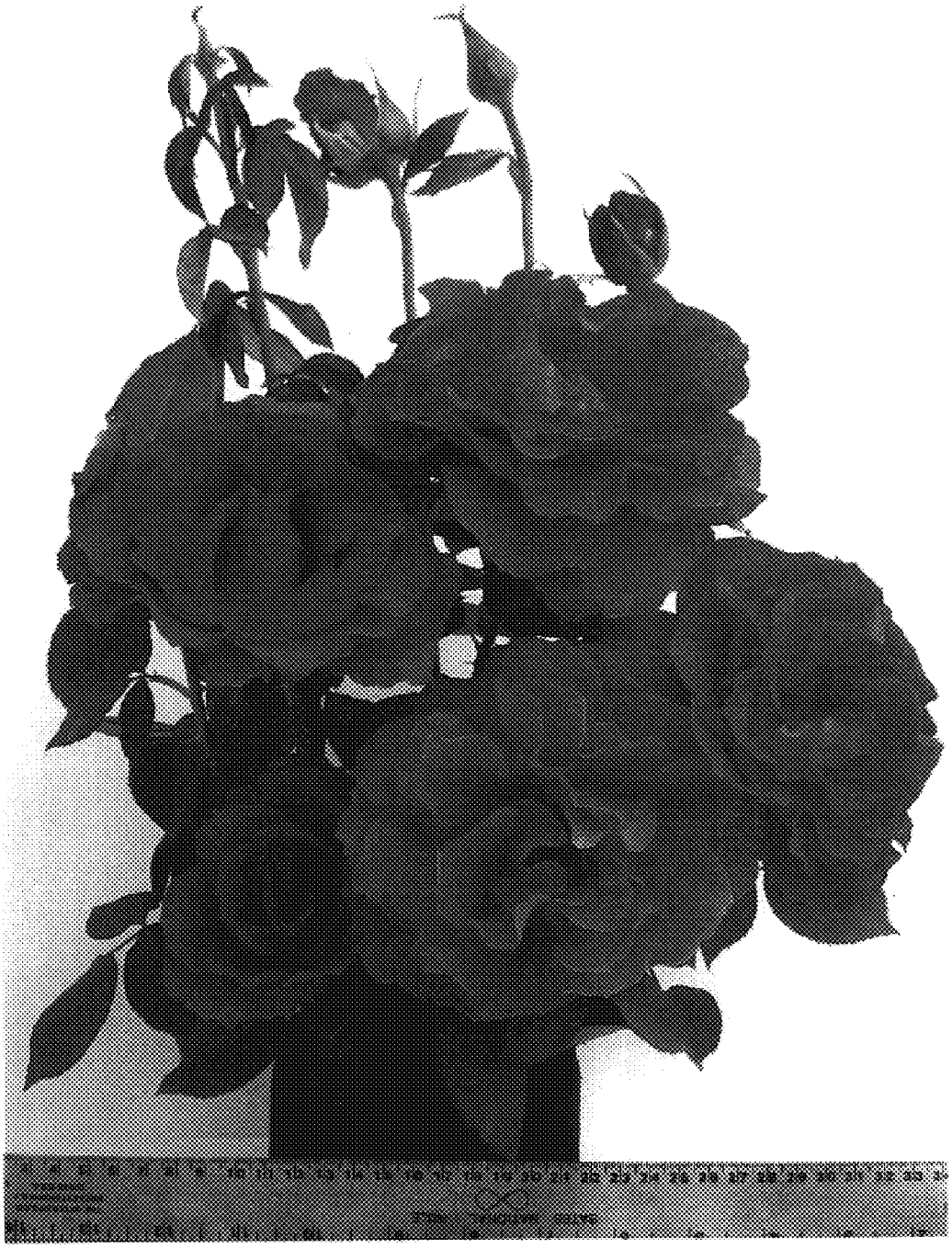

* * * * *